United States Patent [19]

Rapaport et al.

[11] Patent Number: 5,616,564
[45] Date of Patent: Apr. 1, 1997

[54] ANTIPARASITIC OLIGONUCLEOTIDES ACTIVE AGAINST DRUG RESISTANT MALARIA

[75] Inventors: Eliezer Rapaport, Belmont; Paul C. Zamecnik, Shrewbury, both of Mass.

[73] Assignee: Worcester Foundation for Biomedical Research, Inc., Worcester, Mass.

[21] Appl. No.: 178,450

[22] Filed: Jan. 7, 1994

Related U.S. Application Data

[63] Continuation of Ser. No. 815,393, Dec. 31, 1991, abandoned.

[51] Int. Cl.$^6$ .............................. A61K 48/00; C12A 1/68; C12N 5/10; C07H 21/04
[52] U.S. Cl. .............................. 514/44; 435/6; 536/23.1; 536/24.3; 536/24.31; 536/24.32; 536/24.33; 536/24.5; 536/25.1
[58] Field of Search .............................. 514/44; 536/24.5, 536/23.1, 24.3, 24.31, 24.32, 24.33, 25.1; 435/6, 240.2; 935/3, 8, 34, 36

[56] References Cited

U.S. PATENT DOCUMENTS 4,806,463  2/1989  Goodchild et al. .............................. 435/5

FOREIGN PATENT DOCUMENTS

WO9000624  1/1990  WIPO .............................. C12Q 1/68

OTHER PUBLICATIONS

R. Barker et al. PNAS (Jan. '96) 93:514–8.
A. Storey et al. Nucleic Acids Research, vol. 19 (15) ('91) pp. 4109–4114.
J. Holt et al. PNAS, vol. 83 (Jul. 1986) pp. 4784–4798.
M. Cooney et al. Science, vol. 241 (Jul. 22, 1988) pp. 456–459.
C. Hélène et al. Biochimie, vol. 67 ('85) pp. 777–783.
L. Miller et al. Science, vol. 264, (24 jun. '94) pp. 1878–1883.
C. Stein et al. Science, vol. 261 (20 Aug. '93) pp. 1004–1012.
R. Weiss, Science News, vol. 139 (Feb. 16, 1991) pp. 108–109.
W. Marshall et al. Science, vol. 259 (Mar. 12, 1993) pp. 1564–1570.
D. Tidd, Anticancer Res., vol. 10 ('90) pp. 1169–1182.
W. James Antiviral Chem. & Chemotherapy, vol. 2(4)('91) pp. 191–214.
G. Snousnov Mol. Biochem. Parasitology, vol. 58 ('93) pp. 283–292.
P. Westermann et al. Biomed., Bochim. Acta, vol. 48 #1 (1989) pp. 85–93.
P. Verspieren et al. Gene, vol. 61 ('87) pp. 307–315.
T. Le Doan et al. Bulletin of Cancer, vol. 76 ('89) pp. 849–852.
E. Wickstrom, J. Biochem. & Biophys. Methods, vol. 13 ('86) pp. 97–102.
G. Butcher Parasitology, vol. 98 ('89) pp. 315–327.
Ghosh et al. Nucleic Acids Res., vol 21 #24 ('93) pp. 5761–5766.
Uhlmann, E. et al. Chemical Reviews (Jun. 1990) 90: 544–584.
Trager and Jensen, Science 193, 673–675 (1976).
Desjardins et al., Antimicrobial Agents and Chemotherapy 16, 710–718 (1979).
Chulay et al., Experimental Parasitology 55, 138–146 (1983).
Lambros and Vanderburg, J. of Parasitology. 65, 418–420 (1979).
Bitonti et al., Science 242, 1301–1303 (1988).
Martin et. al., Science 235, 899–901 (1987).
Holder et al., Nature 317, 270–273 (1985).
Hadley et al., Ann. Rev. Microbial. 40, 451–477 (1986).
Queen et al., Antimicrobial Agents and Chemotherapy 34, 1393–1398 (1990).
Ferone et al., Molecular Pharmacolgy 5, 49–59 (1969).
Hitchings and Burchell, Advances in Enzymology, 27, 417–468 (1967).
Peterson et al., Proc. Natl. Acad. Sci. U.S.A. 85, 9114–9118 (1988).
Shanzer et al., Proc. Natl. Acad. Sci. U.S.A. 88, 6585–6589 (1991).
Zamecnik and Stephenson, Proc. Natl. Acad. Sci. U.S.A. 75, 280–284 (1978).
Stephenson and Zamecnik, Proc. Natl. Acad. Sci. U.S.A. 75, 285–288 (1978).
Zamecnik et al., Proc. Natl. Acad. Sci. U.S.A. 83, 4143–4146 (1986).
Matsukura et al., Proc. Natl. Acad. Sci. U.S.A. 84, 7706–7710 (1987).
Agrawal et al., Proc. Natl. Acad. Sci. U.S.A. 85, 7079–7084 (1987).
Sarin et al., Proc. Natl. Acad. Sci. U.S.A. 85, 7448–7451 (1988).
Bzik et al., Proc. Natl. Acad. Sci. U.S.A. 84, 8360–8364 (1987).
Sartorius and Franklin, Nucleic Acids Res. 19, 1613–1618 (1991).
Webster et al., Pharmacological Basis of Therapeutics, 954–959 (1990).
Kouni, Biochemical Pharmacology 41, 815–820 (1991).
Agrawal et al., Proc. Natl. Acad. Sci. U.S.A. 86, 7790–7794 (1989).
Agrawal, Prospects for Antisense Nuclei Acid Therapy of Cancer and Aids (1990).
Uhlmann and Peyman, Chemical Reviews 90, 543 (1990).
Hughes et al., Mol. and Biochem. Parasitology 34, 155–166 (1989).
Verspieren et al., Nucleic Acids Res. 18, 4711–4717 (1990).
Tanabe et al., J. Mol. Biol. 195, 273–287 (1987).
Simons et al., Nature 359, 67–70 (1992).
Rapaport et al., Proc. Natl. Acad. Sci. USA 89, 8577–8580 (1992).
Sartorius and Franklin, Parasitology Today 7, 90–93 (1991).
Dix et al., J. Cell Biochem. 41, Supp. O, p. 133 (1989).

Primary Examiner—Charles C. P. Rories
Attorney, Agent, or Firm—Michael S. Greenfield; McDonnell Boehnen Hulbert & Berghoff

[57] ABSTRACT

The invention provides methods and materials for antisense oligonucleotide therapy against active pathogenic infection by drug resistant or drug sensitive pathogens, including *Plasmodium falciparum*.

44 Claims, No Drawings

ANTIPARASITIC OLIGONUCLEOTIDES ACTIVE AGAINST DRUG RESISTANT MALARIA

This application is a continuation of application Ser. No. 07/815,393, filed Dec. 31, 1991, now abandoned.

BACKGROUND OF THE INVENTION

1. Field of the Invention

The invention relates to the treatment of parthogenic infections through the use of chemotherapeutic agents. More specifically, the invention relates to the treatment of infections by parthogens having resistance to conventional chemotherapeutic agents, such as drug resistant malaria.

2. Summary of the Related Art

Malaria is one of the most widespread of human pathogenic diseases, accounting for high morbidity and mortality, particularly in Southeast Asia, Africa and South America. Partial success in the eradication of this disease has been obtained by control of mosquito populations, institution of vaccination programs and treatment with antimalarial drugs. However, multiple resistance to antimalarial drugs has been largely responsible for a resurgence in the incidence and severity of this disease in recent years. Oaks et al., "Malaria, Obstacles and Opportunities, A report of the committee for the study on malaria prevention and control: status review and alternative strategies", Division of International Health, Institute of Medicine, National Academy Press (1991) discloses up to date information about the disease, its clinical aspects, its etiological agent and vector, as well as current difficulties in controlling the disease and other aspects of the present spread of malaria.

Malaria is just one of a variety of human parasitic infections having increased prevalence worldwide. Webster, in Section X of The Pharmacological Basis of Therapeutics, (Gilman et al., Eds.) Eight Edition, Pargamm Press (1991) discusses several factors responsible for the increase in parasitic infections generally, including population growth and crowding, poor sanitation, inadequate control of parasite vectors, introduction of agricultural water control systems, increased population migration, and development of resistance to agents used for chemotherapy or for control of vectors. In fact, acquired drug resistance has become a major public health problem concerning a variety of infectious pathogens, including bacteria and viruses.

Laboratory techniques for in vitro screening of antimalarial drugs are well known in the art. Such techniques utilize the asexual erythrocytic cycle of *Plasmodium falciparum* in cultured human red blood cells. Trager and Jensen, Science 193: 673–675 (1976) discloses continuous maintenance of human malarial parasites in vitro. Desjardins et al., Antimicrobial Agents and Chemotherapy 16: 710–718 (1979) discloses a method of quantitative assessment of the in vitro antimalarial activity of drugs, using a semiautomated microdilution technique. Chulay et al., Experimental Parasitology 55: 138–146 (1983) discloses a method of assessing in vitro growth of *P. falciparum* by measuring incorporation of [$^3$H]-hypoxanthine. Lambros and Vanderburg, Journal of Parasitology 65: 418–420 (1979) discloses procedures for the synchronization of the erythrocytic stages of *P. falciparum* in culture, which allows mechanistic interpretation of the activities of antimalarial drugs.

These in vitro systems have been shown to be predictive of the clinical outcome for a variety of agents in the treatment of human malaria. Bitonti et al., Science 242: 1301–1303 (1988) discloses correct in vitro prediction of reversal of chloroquine resistance in *P. falciparum* by desipramine. Martin et al., Science 235: 899–901 (1987) discloses correct in vitro prediction of chloroquine resistance in *P. falciparum* by verapimil.

A variety of antimalarial agents have been developed. These agents act on the asexual erythrocytic stages as schizonticidal agents. Chloroquine, quinine, quinidine, mefloquine and pyrimethamine are weak bases that accumulate to high levels in the acidic food vacuoles of the plasmodial parasite and interfere with a variety of cellular processes of the parasite, as well as with its interaction with its erythrocytic host. These agents can be used in conjunction with sulfonamides, sulfones, or tetracyclines. Specific inhibition of the malarial parasite can be attempted through exploitation of a variety of potential targets. Holder et al., Nature 317: 270–273 (1985) discloses the primary structure of the precursor to the three major surface antigens of the *P. falciparum* merozoites, the form of the malarial parasite that breaks out of the erythrocyte and invades uninfected erythrocytes. Hadley et al., Ann. Rev. Microbial. 40: 451–477 (1986) discusses the cellular and molecular basis of the invasion of erythrocytes by malaria parasites. Queen et al., Antimicrobial Agents and Chemotherapy 34: 1393–1398 (1990) discusses in vitro susceptibility of *P. falciparum* to compounds that inhibit nucleotide metabolism, a susceptibility grounded in the exclusive reliance of *P. falciparum* on a salvage pathway for obtaining purine bases and nucleosides, and upon de novo synthesis of pyrimidines. Ferone et al., Molecular Pharmacology 5: 49–59 (1969) and Hitchings and Burchell, Advances in Enzymology 27: 417–468 (1967) teach that pyrimethamine inhibits protozoal dihydrofolate reductase, and thus de novo pyrimidine biosynthesis, to a much greater extent than it inhibits the mammalian dihydrofolate reductase of the host, thus making pyrimethamine a useful chemotherapeutic against malaria.

Unfortunately, drugs such as pyrimethamine are rendered ineffective by the global emergence of resistant strains. Peterson et al., Proc. Natl. Acad. Sci. USA 85: 9114–9118 (1988) discloses that a point mutation in dihydrofolate reductase-thymidilate synthase confers resistance to pyrimethamine in falciparum malaria. Martin et al., Science 235: 899–901 (1987) teaches that chloroquine resistance in *P. falciparum* arises from the acquired ability of the parasite to prevent intracellular accumulation of the cytotoxic drug. Multiple drug resistance poses a serious clinical problem for treatment of malaria only with the malarial strain *P. falciparum*. However, this species accounts for over 85% of the cases of human malaria and for most of the mortality resulting from this disease. Shanzer et al., Proc. Natl. Acad. Sci. USA 88: 6585–6589 (1991) teaches that the resistant parasites maintain their cross-resistance towards a variety of drugs in vitro, as well as in vivo, thus enabling investigators to attempt to identify the biochemical mechanisms underlying drug resistance, and to try to overcome such resistance by innovative chemotherapeutic strategies.

There is, therefore, a need for novel chemotherapeutic approaches for the treatment of drug resistant parasites, such as *P. falciparum*. Such approaches can be useful also in the treatment of other protozoan infections, including leishmaniasis and trypanosomiasis.

Exogenous administration of synthetic oligonucleotides is an emerging approach for inhibiting a variety of infectious agents. Zamecnik and Stephenson, Proc. Natl. Acad. Sci. USA 75: 280–284 (1978) discloses inhibition of replication and gene expression of Rous Sarcoma Virus (RSV) by exogenous oligonucleotides in tissue cultures of chick embryo fibroblasts, thereby preventing transformation of fibroblasts into sarcoma cells. Stephenson and Zamecnik, Proc. Natl. Acad. Sci. USA 75: 285–288 (1978) teaches that the same oligonucleotide inhibits cell-free synthesis of proteins specified by the RSV 305 RNA in a reticulocyte system. Zamecnik et al., Proc. Natl. Acad. Sci. USA 83:4143–4146 (1986) discloses inhibition of replication of human immunodeficiency virus (HIV) in vitro screening systems, using synthetic oligonucleotides that are complementary to a variety of conserved regions of the HIV genome. The use of modified internucleotide bridging phosphates resulted in a 10 to 100-fold decrease in the 50% inhibitory concentration ($IC_{50}$) for in vitro HIV replication. Matsukura et al., Proc. Natl. Acad. Sci. USA 84: 7706–7710 (1987) discloses this effect using oligonucleotide phosphorothioates. Agrawal et al., Proc. Natl. Acad. Sci. USA 85: 7079–7084 (1988) shows a similar effect for oligonucleotide phosphorothioates and phosphoroamidates. Sarin et al., Proc. Natl. Acad. Sci. USA 85: 7448–7451 (1988) discloses enhanced inhibition of HIV, using oligonucleotide methylphosphonates.

The use of exogenous oligonucleotides to inhibit retroviral infection, as disclosed in the above publications and in Goodchild et al., U.S. Pat. No. 4,806,463, represents treatment of a latent or dormant condition, since the retroviral genome is integrated into the host cell genome and is expressed with the participation of host cellular enzymes and factors only after a significant latency period. In contrast, the treatment of malaria, other infectious parasitic diseases and acute viral and bacterial infections represents chemotherapy for active infections requiring immediate treatment. Bzik, et al., Proc. Natl. Acad. Sci. USA 84: 8360–8364 (1987) teaches the nucleotide sequence of the *P. falciparum* dihydrofolate reductase-thymidilate synthese gene. However, recent attempts at using exogenous oligonucleotides to inhibit synthesis of these proteins from *P. falciparum* mRNA in a cell free translation system have shown an absence of promise for this approach for the clinical treatment of malaria. Sartorius and Franklin, Nucleic Acids Res. 19: 1613–1618 (1991) demonstrates a complete failure of oligonucleotides to inhibit protein synthesis in such a system, unless the oligonucleotides are pro-annealed to *P. falciparum* mRNA at an elevated temperature of 65° C. for 5 minutes, followed by a one hour cooling at 30° C. Moreover, even under these highly nonphysiological conditions a dramatically high concentration of 150–170 μM was required for the 30–49 nucleotide oligomers to produce 50% inhibition. These results suggest that inhibition of malarial protein synthesis by oligonucleotides will not be possible in vivo, where the host erythrocyte and the intraerythrocytic parasite are maintained at the body temperature of 37° C.

BRIEF SUMMARY OF THE INVENTION

The invention relates to the chemotherapeutic treatment of pathogenic infections. The invention provides methods and materials for antisense oligonucleotide therapy for the treatment of active infections by human pathogens. The method according to the invention comprises administering oligonucleotides that inhibit the pathogenic infection. The method is equally effective in treating drug resistant and drug sensitive pathogens. In particular, the method is highly effective against drug resistant and drug sensitive parasites, such as the malarial parasite. Oligonucleotides according to the invention are useful in the method of the invention. Such oligonucleotides have inhibitory effects upon the pathogen. Preferably, the inhibitory effect of oligonucleotides according to the invention arises from such oligonucleotides having a nucleotide sequence that hybridizes under physiological conditions to a vital gene of the pathogen, such as the P195 and dihydrofolate reductase-thymidilate synthese gene of *Plasmodium falciparum*. In some instances the inhibitory effect of oligonucleotides is independent of any known complementarity to vital genes of the pathogen. Oligonucleotides according to the invention may be conventional oligodeoxynucleotides, or may have one or more modifications at internucleoside linkages or at either end.

DETAILED DESCRIPTION OF THE SPECIFIC EMBODIMENTS

The invention relates to the chemotherapeutic treatment of active infections by pathogenic organisms. More particularly, the invention provides methods and materials for the chemotherapeutic treatment of active infections by human pathogens. The method according to the invention is known as antisense oligonucleotide therapy. The materials according to the invention are oligodeoxynucleotides, oligonucleotide phosphorothioates, other oligonucleotides having modified internucleotide linkages, and modified versions of oligodeoxynucleotides and oligodeoxynucleotide phosphorothioates, and other oligonucleotides having modified internucleotide linkages. For purposes of the invention, the term oligonucleotide includes oligoribonucleotides, oligodeoxyribonucleotides, and oligoribonucleotides or oligodeoxyribonucleotides having modified internucleoside linkages.

In a first aspect, the invention provides, for the first time, methods for treating malaria using antisense oligonucleotide therapy. Antisense oligonucleotide therapy involves the provision to the infected cells of oligonucleotides having a nucleotide sequence that hybridizes under physiological conditions to a target sequence, thereby interfering with the physiological function of that target sequence. In the case of malaria, two genetic targets from *Plasmodium falciparum* were used. The first of these was the P195 gene, which encodes the protein precursor of three smaller proteins which are major surface antigens of merozoites, and thus are required for the development of plasmodial merozoites. Merozoites are the form of the material parasite that breaks out of the erythrocyte and invades uninfected erythrocytes. The P195 sequences used included the first 21 nucleotides of the open reading frame, starting with the AUG start codon (P195-I), and an 18 nucleotide sequence encoding part of an alternate repeat of two tripeptide sequences occurring six and five times respectively in the protein sequence (P195-II). The second genetic target was the dihydrofolate reductase-thymidilate synthase gene, a gene essential to de novo pyrimidine synthesis. Malarial parasites rely exclusively on de novo synthesis of pyrimidine nucleotides, and are incapable of salvaging preformed pyrimidine bases or nucleosides. Consequently, interference with the physiological function of this enzyme is fatal to the malarial parasite.

Those skilled in the art will recognize that other oligonucleotides, having sequences that hybridize under physiological conditions to other portions of the P195 gene or the dihyrdofolate reductase-thymidilate synthase gene will also be useful in the method of the invention, given the success of the oligonucleotides described above. In addition, this success will lead those skilled in the art to recognize that oligonucleotides having a nucleotide sequence that hybridizes under physiological conditions to any vital gene of the malarial parasite will satisfy the requirements of this aspect of the invention. For purposes of the invention, a vital gene is any gene having a physiological function necessary to the replication or reproduction of the pathogen, such that interference with its function by antisense oligonucleotides will impair the ability of the pathogen to replicate or reproduce.

In this aspect of the invention, antisense oligonucleotide therapy was found to be effective in inhibiting malaria in vitro. However, the in vitro system used in these studies has been validated as a predictor of the clinical success of a variety of antimalarial agents. Thus, this aspect of the invention provides an effective method for inhibiting malaria either in vitro, or in vivo. For in vivo treatment, oligonucleotides can be delivered by infusion, injection, oral provision, or topical application.

In a second aspect, the invention provides a method for treating infections by pathogens that have acquired resistance to conventional chemotherapeutic agents. Conventional chemotherapeutic agents are those well known agents that are commonly used to treat the particular pathogen in question. Resistance to chemotherapeutic agents can arise from mutations in the gene encoding the protein upon which the chemotherapeutic agent acts. Alternatively, such resistance can arise from the pathogen being able to prevent intracellular accumulation of the cytotoxic drug. The method according to the invention overcomes both types of resistance, because oligonucleotides act at the level of the gene or mRNA, rather than protein, and because they are not excluded from intracellular accumulation. In this aspect, it was found that the method according to the invention was equally effective against either chloroquine sensitive or chloroquine resistant P. falciparum. Since chloroquine resistance in malaria is generally part of a broad cross-resistance to a variety of chemotherapeutic agents, the invention provides an effective method for overcoming drug resistance in malaria. Moreover, Webster et al., in the Pharmacological Basis of Therapeutics, pp. 954–959 (1990) teaches that parasitic infections in man share many common features, and several antiparasitic agents act against a variety of human parasites. In particular, Kouni, Biochemical Pharmacology 41: 815–820 (1991) demonstrates cross-effectiveness against schistosomiasis, malaria and trypanosomiasis. Thus the invention provides methods for treatment that should be equally effective against either drug sensitive or drug resistant forms of a variety of parasites, including protozoa such as leishmania and trypanosoma, and nonprotozoa parasites, such as schistosoma. Finally, the known mechanisms of drug resistance suggest that oligonucleotides should be useful in methods for treatment that overcomes drug resistance generally. Drug resistance by other pathogens also generally relies upon either modification of the protein acted upon by the drug, or upon the ability to prevent intracellular accumulation of the drug. Oligonucleotides are not rendered ineffective by these mechanisms. Thus, the invention provides a general method of treating drug resistant pathogens, including drug resistant bacteria (e.g., tuberculosis) and viruses.

In a third aspect, the invention provides a method for treating malaria that is safer than existing methods. For example, chloroquine treatment of malaria requires administration of concentrations of chloroquine approaching levels at which significant toxic side effects occur. In contrast, in the method according to the invention, 50% inhibition of malaria is observed at a concentration of oligonucleotide that is over 50-fold lower than is required to produce toxic side effects in rats and mice. Those skilled in the art will recognize that the effectiveness of oligonucleotides may be enhanced by co-treatment of the parasitic infection by oligonucleotides and conventional antimalarial chemotherapeutic agents, such as chloroquine, quinine, quinidine, mefloquine, or pyrimethamine, either with or without sulfonamides, sulfones, or tetracyclines. Such co-treatment should allow reduced doses of the existing chemotherapeutic agents to be used, thereby increasing safety.

In a fourth aspect, the invention provides oligonucleotides that are useful in the method according to the invention. Such oligonucleotides have nucleotide sequences that hybridize under physiological conditions with a vital gene of the pathogen. Examples of such oligonucleotides are oligonucleotides having nucleic acid sequences that hybridize under physiological conditions with the P. falciparum P195 or dihydrofolate reductase-thymidilate synthase genes. Such oligonucleotides are illustrated by way of example in Table I. Oligonucleotides according to the invention may be conventional oligodeoxynucleotides, or may have one or more internucleoside linkages in a modified form such as phosphorothioate, phosphorodithioate or phosphoramidate linkages. In a preferred embodiment, the oligonucleotide has phosphorothioate internucleoside linkages. In addition, oligonucleotides according to the invention may have additional modifications, including the presence of chemical structures that confer resistance to degradation at either or both ends. In a preferred embodiment, the oligonucleotide is rendered resistant to nucleolytic degradation, and hence more effective against malaria, due to the presence of a phosphorbutylamidate as the 3'-most internucleoside linkage.

In a fifth aspect, the invention provides novel oligonucleotides having antimalarial activity that appears to be independent of complementarity to any known vital gene of the malarial parasite. An example of such an oligonucleotide was synthesized as an apparently random oligonucleotide having the nucleotide sequence 5'-CTTGGCAGCT-GCGCGTGACAT-3' (SEQ ID NO. 1). The mechanism of the antimalarial activity of this oligonucleotide is not understood.

Further preferred embodiments of the invention will become apparent from the following examples, which are intended to more fully illustrate the invention, and not to limit its scope.

EXAMPLE 1

Synthesis of Oligodeoxynucleotides,
Oligonucleotide Phosphorothioates and
Modifications Thereof Synthesis and purification of oligonucleotides, oligonucleotide phosphorothioates, and modified forms of each was carried out according to the well known H-phosphonate approach, as described in Agrawal et al., Proc. Natl. Acad. Sci. USA 86: 7790–7794 (1989). The nucleotide sequences selected for such synthesis were complementary to the 5' regions of the coding sequences of the P. falciparum P195 and dihydrofolate reductase-thymidilate synthese genes. The sequences of these genes are set forth, respectively, in Holder et al., Nature 317: 270–273 (1985) and in Bzik et al., Proc. Natl. Acad. Sci. USA 84: 8360–8364 (1987). Apparently random oligonucleotide sequences were synthesized for use as controls. The chemical structure and target specificity of the synthetic oligonucleotides are set forth in Table I, below.

TABLE I

Chemical Structure and Target Specificity of Oligonucleotides Tested as Antimalarial Agents

| No. | Sequence, chemical structure and target sequence |
|---|---|
| PSI | 5'-TAA AAA GAA TAT GAT CTT CAT-3' SEQ ID NO 1<br>Oligodeoxynucleotide phosphorothioate complementary in sequence to the first 21 nucleotides of the open reading frame from the start codon of P195 |
| PSII | 5'-AGC AAC TGA GCC ACC TGA-3' SEQ ID NO 2<br>Oligodeoxynucleotide phosphorothiolete complementary in sequence to the 18 nucleotide sequences in P195 coding for the first two tripeptide repeats |
| PNII | 5'-AGC AAC TGA GCC ACC TAG-3' SEQ ID NO 3<br>Oligodeoxynucleotide phosphomorpholidate complementary in sequence to the same sequence in P195 as PSII |
| POII | 5'-AGC AAC TGA GCC ACC TGA-3' SEQ ID NO 4<br>Oligodeoxynucleotide (phosphodiester internucleoside bond) complementary in sequence to the same sequence in P195 as PSII |
| PSIII | 5'-GTC GCA GAC TTG TTC CAT CAT-3' SEQ ID NO 5<br>Oligodeoxynucleotide phosphorothioate having a sequence complementary to the first 21 nucleotides of the open reading frame of Plasmodium falciparum dihydrofolate reductase-thymidylate synthase gene starting with the start codon |
| PSNIII | 5'-GTC GCA GAC TTG TTC CAT CAT-3' SEQ ID NO 6<br>Oligodeoxynuclootide phosphorothioate with the last 3' phosphodiester bond being a phosphorbutylamidate for the inhibition of exonuclease activity, having the same sequence as PSIII |
| RI | 5'-CTT GGC AGC TGC GCG TGA CAT-3' SEQ ID NO 7<br>Oligodeoxynucleotide phosphorothioate of apparently random sequence |
| RII | 5'-ACC TTA TGT ATC ATA CAC ATG-3' SEQ ID NO 8<br>Oligodeoxynucleotide phosphorothioate apparently random sequence |
| RIII | 5'-AAA AAT ATT TAT TTT CTA A-3' SEQ ID NO 9<br>Oligodeoxynucleotide phosphorothioate of apparently random sequence |
| RIV | 5'-CGC GGC GGC CCG CGG CGC CGG-3' SEQ ID NO 10<br>Oligodeoxynucleotide phosphorothioate of apparently random sequence |

EXAMPLE 2

In Vitro Culture and Synchronization of Plasmodium falciparum

The strains of P. falciparum used for assessment of antimalarial activity of oligonucleotides were W2, an Indochina clone exhibiting chloroquine resistance, and D6, a chloroquine sensitive West African clone. Both strains were isolated at the Walter Reed Army Institute of Research, Washington D.C. Both strains were cultured by a modification of the method of Trager and Jensen, Science 193: 673–675 (1976). Parasites were maintained in flasks in an atmosphere of 4% oxygen, 6% carbon dioxide and 90% nitrogen in a 5–8% erythrocytic suspension in complete RPMI 1640 medium supplemented with 3 mg/ml TES sodium salt, 2 mg/ml glucose, 110 µg/ml sodium pyruvate, 300 µg/ml glutamine, 5 µg/ml hypoxanthine, 25 µg/ml gentamicin and 10% human plasma at 37° C. Fresh type A, Rh positive blood cells and human plasma were obtained from the American Red Cross. Synchronization of parasites was performed by treatment with D-sorbitol, according to the well known method of Lambros and Vanderburg, Journal of Parasitology 65: 418–420 (1979).

EXAMPLE 3

Assessment of the Antimalarial Activity of Oligonucleotides

Nonsynchronous cultures of P. falciparum were incubated for 72 hours, the last 48 hours in the presence of oligonucleotides. Synchronized cultures were grown in the presence of oligonucleotides, beginning 24 hours after synchronization by D-sorbitol treatment. Antimalarial activities were quantitatively determined either by counting parasites or by the incorporation of [$^3$H]-hypoxanthine into acid insoluble radioactivity, according to the method of Chulay et al., Experimental Parasitology 55: 138–146 (1983).

For counting of parasites, parasitized erythrocytes (0.5% to 1% parasitemia) were cultured in 48 well microculture plates (Gibco, Chagrin Falls, Ohio) at 5% hematocrit in a total volume of 1 ml per well. Parasitemia levels were determined by counting thin blood films ("smears"), fixed and stained with Diff-Quick™ (Baxter, McGaw Park, Ill.). At least 1000 erythrocytes were counted. Parasites were classified according to their developmental stage as ring forms (R) without pigment, which is the first form after merozoite inversion of the erythrocyte, trophozoites (T) containing pigment and a single nucleus, and schionts (S), which are developmental forms with more than one nucleus.

For incorporation of [$^3$H]-hypoxanthine analysis, [$^3$H]-hypoxanthine was provided either for 24 hours in a complete medium, or for 4 hours in a partially supplemented medium lacking human plasma and unlabelled hypoxanthine. Uninfected erythrocytes, which do not synthesize either RNA or DNA, do not incorporate [$^3$H]-hypoxanthine into acid insoluble radioactivity.

The antimalarial activities of various oligonucleotides at 0.1 µM and 1.0 µM concentration against the chloroquine resistant P. falciparum W2 strain growing nonsynchronously are shown in Table II, below.

TABLE II

Antimalarial activity of oligodeoxynuclotides against chloroquine-resistant *Plasmodium falciparum* W2 (Indochina strain)

| Oligomer | Concentration (µM) | Parasitemia (% parasitized red blood cells) | | | [³H]hypoxanthine incorporation (% of control) |
|---|---|---|---|---|---|
| | | R | T | S | |
| Experiment 1 | | | | | |
| None | | 1.8 | 2.8 | 2.0 | 100 |
| PSI | 0.1 | 0.8 | 2.6 | 1.4 | 121 |
| PSI | 1 | 0.1 | 0.5 | 0.3 | 31 |
| PSII | 0.1 | 0.9 | 1.9 | 1.3 | 110 |
| PSII | 1 | — | 0.4 | 0.3 | 36 |
| POII | 1 | 0.5 | 1.5 | 1.7 | 88 |
| PNII | 1 | 0.7 | 1.6 | 1.8 | 93 |
| RI | 0.1 | 0.7 | 1.3 | 1.5 | 71 |
| RI | 1 | 0.1 | — | 0.1 | 18 |
| RII | 0.1 | 1.1 | 2.3 | 2.1 | 115 |
| RII | 1 | 0.6 | 1.5 | 1.0 | 73 |
| Experiment 2 | | | | | |
| None | | 2.1 | 1.9 | 2.3 | 100 |
| PSIII | 0.1 | 0.9 | 1.7 | 2.0 | 85 |
| PSIII | 1 | 0.2 | 0.6 | 0.1 | 36 |
| PSNIII | 0.1 | 0.7 | 1.1 | 0.9 | 76 |
| PSNIII | 1 | — | 0.3 | 0.2 | 20 |

Parasitemia was determined by counting a total of at least 1000 red blood cells, R, T and S represent the count of rings, trophozoites and schizonts, respectively.

The antimalarial activities of various oligonucleotides at 0.1 and 1.0 µM concentration against the chloroquine resistant *P. falciparum* W2 strain, growing synchronously, are shown in Table III, below.

TABLE III

Antimalarial Effects of Oligodeoxynuclcotides Against Chloroquine-Resistant *Plasmodium Falciparum* W-2 in Synchronous Cultures

| Oligomer | Concentration (µM) | Parasitemia (% parasitized red blood cells) | | | [³H]Hypoxanthine incorporation into schizonts, 72 hrs after D-sorbitol synchronization (% of control) |
|---|---|---|---|---|---|
| | | R | T | S | |
| Experiment 1: 72 hours after synchronization | | | | | |
| None | | 0.2 | 2.6 | 16.1 | 100 |
| PSI | 0.1 | 0.1 | 1.0 | 14.3 | 154 |
| PSI | 1 | — | 0.5 | 3.6 | 43 |
| RI | 0.1 | 0.1 | 0.6 | 10.7 | 68 |
| RI | 1 | — | 0.4 | 2.5 | 26 |
| Chloroquine | 0.1 | — | 0.4 | 0.6 | 2 |
| Experiment 2: Invasion assay, 24 hours treatment (24–48 hours after synchronization) during schizont → rings, transitions, with analysis at 48 hours after synchronization | | | | | |
| None | | 19.0 | 0.4 | — | |
| PSI | 0.1 | 15.6 | 1.3 | 0.1 | |
| PSI | 1 | 5.7 | 1.2 | — | |
| RI | 0.1 | 10.1 | 0.9 | 0.2 | |
| RI | 1 | 3.3 | 0.9 | — | |
| Chloroquine | 0.1 | 14.8 | 1.7 | 0.6 | |
| Experiment 3: Invasion assay, as in Experiment 2 but with different cultures | | | | | |
| None | | 4.9 | 0.7 | — | |
| PSIII | 0.1 | 1.6 | 0.6 | — | |
| PSIII | 1 | 0.6 | 0.3 | — | |
| PSNIII | 0.1 | 1.2 | 0.3 | — | |
| PSNIII | 1 | 0.3 | 0.3 | — | |

The fifty percent inhibition concentration ($IC_{50}$) for various oligonucleotides was determined, and the results are shown for the chloroquine resistant *P. falciparum* strain W2 (Table IV), as well as for the chloroquine sensitive strain D6 (Table V). Chloroquine was used as a control. For these experiments, parasite cultures were synchronized by D-sorbitol treatment. To examine the effect on schizont to ring transition, antimalarial compounds were added for 24 hours, beginning 24 hours after synchronization. To examine the effect on ring to trophozoite to schizont transitions, antimalarial compounds were added for 24 hours, beginning 48 hours after synchronization. Inhibition was measured by [³H]-hypoxanthine incorporation 72 hours after synchronization.

TABLE IV

Antimalarial Activities of Oligodeoxynucleotides Against The Chloroquine-Resistant *Plasmodium falciparum* W2 strain

| Oligomer or Chloroquine (during schizonts to rings transition, 24 to 48 hours after synchronization) | $IC_{50}$ (µM) | Oligomer or Chloroquine (during rings to trophozoites to schizonts transition, 48 to 72 hours after synchronization) | $IC_{50}$ (µM) |
|---|---|---|---|
| PSI | 0.9 | PSI | >2.5 |
| PSII | 1.1 | PSII | >2.5 |
| PSIII | 0.7 | PSIII | >2.5 |
| PSNIII | 0.5 | PSNIII | >2.5 |
| RI | 0.5 | RI | >2.5 |
| RIII | >5.0 | RIII | >5.0 |
| RIV | >5.0 | RIV | >5.0 |
| Chloroquine | 0.065 | Chloroquine | 0.050 |

TABLE V

Antimalarial Activities of Oligodeoxynucleotides Against The Chloroquine-Sensitive *Plasmodium falciparum* D6 strain

| Oligomer or Chloroquine (during schizonts to rings transition, 24 to 48 hours after synchronization) | $IC_{50}$ (µM) | Oligomer or Chloroquine (during rings to trophozoites to schizonts transition, 48 to 72 hours after synchronization) | $IC_{50}$ (µM) |
|---|---|---|---|
| PSI | 0.9 | PSI | >2.5 |
| PSII | 0.9 | PSII | >2.5 |
| PSIII | 0.8 | PSIII | >2.5 |
| PNIII | 0.5 | PSNIII | >2.5 |

TABLE V-continued

Antimalarial Activities of Oligodeoxynucleotides Against The Chloroquine-Sensitive *Plasmodium falciparum* D6 strain

| Oligomer or Chloroquine (during schizonts to rings transition, 24 to 48 hours after synchronization) | $IC_{50}$ (μM) | Oligomer or Chloroquine (during rings to trophozoites to schizonts transition, 48 to 72 hours after synchronization) | $IC_{50}$ (μM) |
| --- | --- | --- | --- |
| RI | 0.7 | RI | >2.5 |
| RIII | >5.0 | RIII | >5.0 |
| RIV | >5.0 | RIV | >5.0 |
| Chloroquine | 0.015 | Chloroquine | 0.004 |

These results indicate that oligonucleotide phosphorothioates are equally effective in inhibiting the growth and invasion of chloroquine resistant and chloroquine sensitive strains of *P. falciparum*. The results shown in Tables IV and V further suggest that the tested oligonucleotides interfere with schizont maturation, merozoite release, merozoite attachment to erythrocytes, merozoite invasion of erythrocytes, or ring formation. This is in contrast to chloroquine, which is a known schizonticidal agent. Although chloroquine inhibited even the chloroquine resistant strain W2 at the high concentrations shown in Table IV, such concentrations cannot be used in vivo because of significant toxic side effects. In contrast, the $IC_{50}$ for oligonucleotides shown in Tables IV and V is at least 50 times lower than the concentration reported to cause toxic effects in rats and mice (see Agrawal, In: Prospects for Antisense Nucleic Acid Therapy of Cancer and AIDS (E. Wickstrom, Ed.), Wiley-Liss, Inc., pp. 143–158 (1990)).

All tested oligonucleotide phosphorothioates having a complementary sequence to segments of the malarial genome exhibited antimalarial activity. Interestingly, one of the apparently random oligonucleotides tested showed significant antimalarial activity. The mechanism of this inhibition is not known. Higher antimalarial activity was observed for an oligonucleotide having a butyl phosphoramidate group at the last internucleotide phosphate moiety of the 3' end and (PSNIII) than for an oligonucleotide of identical sequence, but lacking the butyl phosphoramidate group (PSIII). This chemical modification inhibits exonucleolytic degradation of the oligonucleotide, thus giving increased antimalarial activity as a product of increased oligonucleotide stability.

Oligonucleotides were taken up by parasitized erythrocytes, but were not taken up by uninfected erythrocytes (data not shown), suggesting that oligonucleotides can be used for intravascular treatment of infectious diseases in which the only association sought is that of the oligonucleotide with the infected cell. Similar alteration of the permeability functions of a host cell carrying an infectious agent has been described for viral diseases in Virology (Fields and Knips, Eds.) Raven Press, New York (1990). This result suggests that oligonucleotides can be used for systemic treatment of pathogenic infections generally, i.e., for parasitic viral and bacterial infections.

We claim:

1. An antimalarial oligonucleotide comprising one or more phosphorothioate internucleotide linkages and consisting of the nucleotide sequence shown as TAAAAAGAATATGATCTTCAT (SEQ ID NO: 1), AGCAACTGAGCCACCTGA (SEQ ID NO: 2), or CTTGGCAGCTGCGCGTGACACAT (SEQ ID NO: 7).

2. The compound according to claim 1, wherein the oligonucleotide has one or more modified internucleotide linkage which is not phosphorothioate.

3. The compound according to claim 2, wherein the modified internucleotide linkage is selected from the group consisting of phosphorodithioate, phosphomorpholidate, and phosphoroamidate.

4. The compound according to claim 1, wherein the oligonucleotide has a chemical structure at either or both ends to prevent nucleolytic degradation.

5. The compound according to claim 2, wherein the oligonucleotide has a chemical structure at either or both ends to prevent nucleolytic degradation.

6. The compound according to claim 3, wherein the oligonucleotide has a chemical structure at either or both ends to prevent nucleolytic degradation.

7. An antimalarial oligonucleotide comprising one or more phosphorothioate internucleotide linkages and consisting of a nucleotide sequence that is complementary to the mRNA of a gene essential to the growth or reproduction of drug-resistant *Plasmodium falciparum*, which oligonucleotide is taken up by parasitized erythrocytes and inhibits the growth or reproduction of drug-resistant *Plasmodium falciparum*.

8. The antimalarial oligonucleotide according to claim 7, wherein the oligonucleotide has a chemical structure at either or both ends that renders the oligonucleotide resistant to nucleolytic degradation.

9. The antimalarial oligonucleotide according to claim 7, wherein the oligonucleotide has one or more modified internucleotide linkage which is not phosphorothioate.

10. The antimalarial oligonucleotide according to claim 9, wherein the modified internucleotide linkage is selected from the group consisting of phosphorodithioate and phosphoramidate internucleotide linkages.

11. An antimalarial oligonucleotide comprising one or more phosphorothioate internucleotide linkages and consisting of a nucleotide sequence that is complementary to the mRNA of a gene essential to the growth or reproduction of drug-resistant *Plasmodium falciparum*, which oligonucleotide is taken up by parasitized erythrocytes and inhibits the growth or reproduction of *Plasmodium falciparum*.

12. The antimalarial oligonucleotide according to claim 11, wherein the oligonucleotide has a chemical structure at either or both ends that renders the oligonucleotide resistant to nucleolytic degradation.

13. The antimalarial oligonucleotide according to claim 11, wherein the oligonucleotide has one or more modified internucleotide linkage which is not phosphorothioate.

14. The antimalarial oligonucleotide according to claim 13, wherein the modified internucleotide linkage is selected from the group consisting of phosphorodithioate and phosphoramidate internucleotide linkages.

15. An antimalarial oligonucleotide comprising one or more phosphorothioate internucleotide linkages and consisting of a nucleotide sequence that is complementary to the mRNA of a *Plasmodium falciparum* P195 gene, which oligonucleotide is taken up by parasitized erythrocytes and inhibits the growth or reproduction of *Plasmodium falciparum*.

16. The antimalarial oligonucleotide according to claim 15, wherein the oligonucleotide has a chemical structure at either or both ends that renders the oligonucleotide resistant to nucleolytic degradation.

17. The antimalarial oligonucleotide according to claim 15, wherein the oligonucleotide has one or more modified internucleotide linkage which is not phosphorothioate.

18. The antimalarial oligonucleotide according to claim 7, wherein the modified internucleotide linkage is selected from the group consisting of phosphorodithioate and phosphoramidate internucleotide linkages.

19. An antimalarial oligonucleotide comprising one or more phosphorothioate internucleotide linkages and consisting of a nucleotide sequence that is complementary to the mRNA of a *Plasmodium falciparum* dihydrofolate reductase-thymidilate synthase gene, which oligonucleotide is taken up by parasitized erythrocytes and inhibits the growth or reproduction of *Plasmodium falciparum*.

20. The antimalarial oligonucleotide according to claim 19, wherein the oligonucleotide has a chemical structure at either or both ends that renders the oligonucleotide resistant to nucleolytic degradation.

21. The antimalarial oligonucleotide according to claim 19, wherein the oligonucleotide has one or more modified internucleotide linkage which is not phosphorothioate.

22. The antimalarial oligonucleotide according to claim 21, wherein the modified internucleotide linkage is selected from the group consisting of phosphorodithioate and phosphoroamidate internucleotide linkages.

23. A method of inhibiting the growth and reproduction of *Plasmodium falciparum* comprising contacting a *Plasmodium falciparum* infected erythrocyte with an oligonucleotide according to claim 1.

24. A method of inhibiting the growth and reproduction of *Plasmodium falciparum* comprising contacting a *Plasmodium falciparum* infected erythrocyte with an oligonucleotide according to claim 2.

25. A method of inhibiting the growth and reproduction of *Plasmodium falciparum* comprising contacting a *Plasmodium falciparum* infected erythrocyte with an oligonucleotide according to claim 3.

26. A method of inhibiting the growth and reproduction of *Plasmodium falciparum* comprising contacting a *Plasmodium falciparum* infected erythrocyte with an oligonucleotide according to claim 4.

27. A method of inhibiting the growth and reproduction of *Plasmodium falciparum* comprising contacting a *Plasmodium falciparum* infected erythrocyte with an oligonucleotide according to claim 5.

28. A method of inhibiting the growth and reproduction of *Plasmodium falciparum* comprising contacting a *Plasmodium falciparum* infected erythrocyte with an oligonucleotide according to claim 6.

29. A method of inhibiting the growth and reproduction of drug-resistant *Plasmodium falciparum* comprising contacting a *Plasmodium falciparum* infected erythrocyte with an oligonucleotide according to claim 7.

30. A method of inhibiting the growth and reproduction of drug-resistant *Plasmodium falciparum* comprising contacting a *Plasmodium falciparum* infected erythrocyte with an oligonucleotide according to claim 8.

31. A method of inhibiting the growth and reproduction of drug-resistant *Plasmodium falciparum* comprising contacting a *Plasmodium falciparum* infected erythrocyte with an oligonucleotide according to claim 9.

32. A method of inhibiting the growth and reproduction of drug-resistant *Plasmodium falciparum* comprising contacting a *Plasmodium falciparum* infected erythrocyte with an oligonucleotide according to claim 10.

33. A method of inhibiting the growth and reproduction of *Plasmodium falciparum* comprising contacting a *Plasmodium falciparum* infected erythrocyte with an oligonucleotide according to claim 11.

34. A method of inhibiting the growth and reproduction of *Plasmodium falciparum* comprising contacting a *Plasmodium falciparum* infected erythrocyte with an oligonucleotide according to claim 12.

35. A method of inhibiting the growth and reproduction of *Plasmodium falciparum* comprising contacting a *Plasmodium falciparum* infected erythrocyte with an oligonucleotide according to claim 13.

36. A method of inhibiting the growth and reproduction of *Plasmodium falciparum* comprising contacting a *Plasmodium falciparum* infected erythrocyte with an oligonucleotide according to claim 14.

37. A method of inhibiting the growth and reproduction of *Plasmodium falciparum* comprising contacting a *Plasmodium falciparum* infected erythrocyte with an oligonucleotide according to claim 15.

38. A method of inhibiting the growth and reproduction of *Plasmodium falciparum* comprising contacting a *Plasmodium falciparum* infected erythrocyte with an oligonucleotide according to claim 16.

39. A method of inhibiting the growth and reproduction of *Plasmodium falciparum* comprising contacting a *Plasmodium falciparum* infected erythrocyte with an oligonucleotide according to claim 17.

40. A method of inhibiting the growth and reproduction of *Plasmodium falciparum* comprising contacting a *Plasmodium falciparum* infected erythrocyte with an oligonucleotide according to claim 18.

41. A method of inhibiting the growth and reproduction of *Plasmodium falciparum* comprising contacting a *Plasmodium falciparum* infected erythrocyte with an oligonucleotide according to claim 19.

42. A method of inhibiting the growth and reproduction of *Plasmodium falciparum* comprising contacting a *Plasmodium falciparum* infected erythrocyte with an oligonucleotide according to claim 20.

43. A method of inhibiting the growth and reproduction of *Plasmodium falciparum* comprising contacting a *Plasmodium falciparum* infected erythrocyte with an oligonucleotide according to claim 21.

44. A method of inhibiting the growth and reproduction of *Plasmodium falciparum* comprising contacting a *Plasmodium falciparum* infected erythrocyte with an oligonucleotide according to claim 22.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TAAAAGAAT ATGATCTTCA T
    2 1

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGCAACTGAG CCACCTGA
    1 8

( 2 ) INFORMATION FOR SEQ ID NO:3:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

AGCAACTGAG CCACCTAG                                         18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGCAACTGAG CCACCTGA                                         18

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTCGCAGACT TGTTCCATCA T                                  21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GTCGCAGACT TGTTCCATCA T                                  21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTTGGCAGCT GCGCGTGACA T                                  21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ACCTTATGTA TCATACACAT G 21

( 2 ) INFORMATION FOR SEQ ID NO:9:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

AAAAATATTT ATTTTCTAA 19

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

CGCGGCGGCC CGCGGCGCCG G 21